United States Patent [19]

Chavez, Jr. et al.

[11] Patent Number: 5,342,541
[45] Date of Patent: * Aug. 30, 1994

[54] PURIFIED HYDROXY-FUNCTIONAL POLYETHER COMPOUNDS

[75] Inventors: Johnny Chavez, Jr., Lake Jackson; Andrew S. Farnum, Angleton; Vaughn M. Nace, Lake Jackson; Raymond A. Plepys, Lake Jackson; Randall K. Whitmire, Lake Jackson; Van A. Kent, Lake Jackson; Paul D. Bettge, Lake Jackson; Hans R. Friedli, Lake Jackson, all of Tex.

[73] Assignee: The Dow Chemical Company, Midland, Mich.

[*] Notice: The portion of the term of this patent subsequent to Mar. 10, 2009 has been disclaimed.

[21] Appl. No.: 329,923

[22] Filed: Mar. 29, 1989

[51] Int. Cl.$^5$ ................................. C09K 3/00
[52] U.S. Cl. ............................. 252/182.27; 568/621
[58] Field of Search .................... 568/621; 252/182.27

[56] References Cited

U.S. PATENT DOCUMENTS

| | | |
|---|---|---|
| 2,780,652 | 2/1957 | Gander . |
| 2,812,360 | 11/1957 | Mills et al. . |
| 2,899,411 | 8/1959 | Schollenberger .................... 568/621 |
| 2,996,550 | 8/1961 | Simons ................................ 568/621 |
| 3,134,814 | 5/1957 | Sargent et al. . |
| 3,271,462 | 9/1966 | Earing . |
| 3,299,151 | 1/1967 | Wismer et al. . |
| 3,441,616 | 4/1969 | Pizzini et al. . |
| 3,833,669 | 9/1974 | Gehm et al. ......................... 568/621 |
| 4,129,718 | 12/1978 | Muzzio . |
| 4,137,398 | 1/1979 | Muzzio . |
| 4,176,218 | 11/1979 | Demou et al. ...................... 252/182 |
| 4,245,077 | 1/1981 | DeMarco . |
| 4,316,991 | 2/1982 | Speranza et al. . |
| 4,323,658 | 4/1982 | Speranza et al. . |
| 4,355,188 | 10/1982 | Herold et al. . |
| 4,359,550 | 11/1982 | Narayan et al. ..................... 252/182 |
| 4,366,326 | 12/1982 | Vodrazka et al. . |
| 4,507,475 | 3/1985 | Straehle et al. . |
| 4,521,572 | 6/1985 | Cuscurida et al. . |
| 4,621,105 | 11/1986 | Stratton et al. . |
| 4,650,909 | 3/1987 | Yoakum . |
| 4,711,910 | 12/1987 | Statton et al. . |
| 4,745,230 | 5/1988 | Offen et al. ......................... 568/621 |
| 4,751,331 | 6/1988 | Efford ................................. 568/621 |
| 4,952,673 | 8/1990 | Mueller .............................. 568/621 |
| 4,967,017 | 10/1990 | Schmid et al. ...................... 568/621 |
| 5,095,061 | 3/1992 | Chavez et al. .................. 252/182.27 |

FOREIGN PATENT DOCUMENTS

| | | |
|---|---|---|
| 634036 | 6/1963 | Belgium . |
| 210460 | 9/1982 | Fed. Rep. of Germany . |
| 61-043629 | 3/1986 | Japan . |
| 61-043629 | 3/1986 | Japan ................................ 568/621 |
| 1019166 | 2/1966 | United Kingdom . |

OTHER PUBLICATIONS

Quantitative Organic Analysis . . . , Fourth Edition, by Sidney Siggia, Ph.D., and J. Gordon Hanna, pp. 510–519 (1988).
Dege et al., *J. Am. Chem. Soc.*, 81, 3374–79 (Jul. 1959).
Gusev et al., *Chem. Abs.*, 84, abs. #84:5421g, 1976.

*Primary Examiner*—Edward A. Miller

[57] ABSTRACT

The concentration of propenyl ethers in a hydroxy-functional polyether having oxypropylene units is reduced by a process including the step of contacting the polyether with an acid ion exchange resin for a time and at a temperature sufficient for the conversion of at least some of the propenyl ethers to propionaldehyde and in the presence of sufficient water for the conversion. Optionally, the polyether is treated with an epoxy compound in an amount sufficient to reduce the acidity of the polyol.

14 Claims, No Drawings

PURIFIED HYDROXY-FUNCTIONAL POLYETHER COMPOUNDS

This invention relates to a process for purification of polyethers, more specifically to a process for purification of hydroxy-functional polyethers.

It has long been recognized that unsaturated compounds occur in polyethers prepared by polymerizing alkylene oxides. When the alkylene ethers include propylene oxide units, 1,2-propenyl ether is among the unsaturated compounds and is indicative of the presence of same. Presence of such unsaturated compounds in polypropylene glycols is discussed by G. J. Dege, R. L. Harris and J. S. MacKenzie in *J. Amer. Chem. Soc.*, 81, p 3374 (1959). In certain polyurethanes prepared from polyether polyols, these unsaturated compounds are believed to cause discoloration, particularly discoloration on heating referred to as scorch. Removal of the unsaturated compounds is, therefore, desirable.

There are variety of means of purifying polyethers. Certain mineral acids are used at various stages of treatment of polyether polyols in processes such as those disclosed in U.S. Pat. Nos. 2,996,550 to Simons; 4,507,475 to Straehle et al. and Japanese J56104936 (J87036052). Water, carbon dioxide and adsorbents such as magnesium silicate are used to remove alkaline catalysts in the process disclosed by Muzzio in 4,129,718. Water, ortho-phosphoric acid and adsorbents such as magnesium silicate are used to remove alkaline catalysts in the process disclosed by Straehle et al in U.S. Pat. No. 4,507,475. Formic acid is used in the process disclosed by Peffer in U.S. Pat. No. 3,299,151. Each of these methods offer certain disadvantages, generally they introduce materials that must be removed from the polyethers.

Some polyether polyol treatments have involved ion exchange resins. Purification of certain polyether polyols has involved water and certain cationic resins as described in Japanese J61043629. In the process described in German 210,460, acid neutralization of catalyst is followed by certain ion exchange resin treatment. A mercury activated sulfonated polystyrene ion exchange resin is used in the process described in U.S. Pat. No. 3,271,462 to Earing. Certain ion exchange resins are optionally used in place of mineral acids for hydrolyzing certain acetals in certain polyols as in the process disclosed by Mills et al. in U.S. Pat. No. 2,812,360. Certain mixed resins are used to treat certain polyethylene glycols for human cell genetic transfection as disclosed in U.S. Pat. No. 4,650,909 to Yoakum. In the process disclosed by U.S. Pat. No. 4,355,188 to Herold et al., a polyol may be ion exchanged or neutralized after a strong base is used to treat polyols formed using metal cyanide complex catalysts.

Acidic ion exchange resins, particularly sulfonic acid ion exchange resins are known to release acids into organic compounds. This phenomenon is discussed, for instance, I. J. Jakovac in *Catalyst Supports and Supported Catalysts*, by A. B. Stiles, Ed., Butterworths, Boston (1987) pp. 190. Acids are, however, detrimental in certain formulations for forming polyurethanes.

In some instances, certain epoxy compounds have been disclosed for removal of certain acids from certain other compounds. In the process disclosed in U.S. Pat. No. 4,164,487 to Martin, certain coating compositions are treated with certain epoxy compounds after treatment with phosphoric acid. Certain anaerobic compositions containing acidic impurities are stabilized by addition of certain epoxy compounds in the process disclosed in U.S. Pat. No. 4,245,077. Certain epoxy compounds are disclosed for treatment of acidity or hydrolyzable chloride in certain isocyanates as disclosed in U.S. Pat. Nos. 3,264,336 to Powers and 3,793,362 to Kolakowski, et al. and East German 238,988. These references, do not, however, teach that epoxy compounds are useful for removing acidic compounds from polyether hydroxyl-containing compounds.

SUMMARY OF THE INVENTION

In one aspect, the invention is a process for reducing the concentration of propenyl ethers in a hydroxy-functional polyether having oxypropylene units by a process including the steps of:

(1) contacting the polyether with an acid ion exchange resin for a time and at a temperature sufficient for the conversion of at least some of the the propenyl ethers to propionaldehyde in the presence of sufficient water for the conversion, and thereafter (2) treating the polyether with an epoxy compound in an amount sufficient to reduce the acidity of the polyol.

In another aspect, the invention is a process for reducing the concentration of propenyl ethers in a hydroxy-functional polyether having oxypropylene units by a process including a step of:

(1) contacting the polyether with a gel-type sulfonic acid ion exchange resin having an aqueous exchange capacity of from about 0.5 to about 5 equivalents/liter for a time and at a temperature sufficient for the conversion of at least some of the the propenyl ethers to propionaldehyde and in the presence of sufficient water for the conversion.

In another aspect, the invention is a process for reducing the acidity of a hydroxy-functional polyether by a process including a step of:

(1) treating the polyether with an epoxy compound in an amount sufficient to reduce the acidity of the polyether.

In yet another aspect, a composition comprising (A) a hydroxy-functional polyether which is the polymerization prepared product of propylene oxide or a mixture of propylene oxide with an alkylene oxide selected from the group consisting of ethylene oxide, butylene oxide and mixtures thereof in the presence of and initiator; and (B) at least one epoxy compound different from ethylene oxide, propylene oxide and butylene oxide.

DETAILED DESCRIPTION OF THE INVENTION

Hydroxy-functional polyethers treated in the practice of this invention are polyalkylene polyethers having at least one hydroxyl group, preferably, polyalkylene polyether polyols. Said polyethers include the polymerization products of oxiranes or other oxygen-containing heterocyclic compounds such as tetramethylene oxide in the presence of a catalyst; and/or initiated by water, polyhydric alcohols having from about two to about eight hydroxyl groups, amines and the like. Preferably, the polyethers have at least some oxypropylene units produced from propylene oxide. The propylene oxide is homopolymerized or copolymerized with one or more other oxiranes or other oxygen-containing heterocyclic compounds. The oxygen-containing heterocyclic compounds are, preferably alkylene oxides.

The oxygen-containing heterocyclic compounds, herein after exemplified by alkylene oxides, are suitably reacted either in mixture or sequentially. When more than one alkylene oxide is used, resulting polyethers can contain random, block or random and block distributions of monomers. Mixtures of alkylene oxides most often produce randomly distributed alkylene oxide units. Sequential addition of different alkylene oxides most often produces blocks of the alkylene oxide segments in a polyether chain.

Exemplary oxiranes suitable for preparation of polyethers include ethylene oxide, propylene oxide, butylene oxide, amylene oxide, glycidyl ethers such as t-butyl glycidyl ether, phenyl glycidyl ether, and the like. Other suitable oxiranes include 1,2-butylene oxide, 1,2-hexylene oxide, 1,2-decene oxide, 2-methoxy propylene oxide, methoxy ethylene oxide, 2,3-butylene oxide, 2,3-hexylene oxide, 3,4-decene oxide, 1,1,1-trifluoromethyl 2,3-epoxyoctane, styrene oxide and the like. The polyethers are also prepared from starting materials such as tetrahydrofuran copolymerized with alkylene oxide; epihalohydrins such as epichlorohydrin, epiiodohydrin, epibromohydrin, 3,3-dichloropropylene oxide, 3-chloro-1,2-epoxypropane, 3-chloro-1,2-epoxybutane, 3,4-dichloro-1,2-epoxybutane, 3,3,3-trichloropropylene oxide and the like; arylalkylene oxides such as styrene oxide and the like. Preferably, the polyethers are prepared from alkylene oxides having from about two to about six carbon atoms such as ethylene oxide, propylene oxide, and butylene oxide. More preferably, the polyethers are prepared from at least about 10, most preferably at least about 50, and even more preferably at least about 80 percent of an alkylene oxide selected from the group consisting of propylene oxide, 1,2-butylene oxide, 2,3-butylene oxide or mixtures thereof. Most preferably, propylene oxide is selected from the group consisting of propylene oxide, 1,2-butylene oxide, 2,3-butylene oxide or mixtures thereof; and preferably, the polyethers are prepared from at least about 10, more preferably at least about 50, and most preferably at least about 80 percent propylene oxide. Homopolymers of propylene oxide, or copolyethers or propylene oxide with ethylene oxide, butylene oxides and mixtures thereof are most preferred for use in the practice of the invention.

Illustrative alcohols suitable for initiating formation of a polyalkylene polyether include glycerine, ethylene glycol, 1,3-propylene glycol, dipropylene glycol, 1,2-propylene glycol, 1,4-butylene glycol, 1,3-butylene glycol, 1,2-butylene glycol, 1,5-pentane diol, 1,7-heptane diol, glycerol, 1,1,1-trimethylolpropane, 1,1,1-trimethylolethane, hexane-1,2,6-triol, alpha-methyl glucoside, pentaerythritol, erythritol, as well as pentols and hexols. Sugars such as glucose, sucrose, fructose, maltose and the like as well as compounds derived from phenols such as (4,4'-hydroxyphenyl)2,2-propane, bisphenols, alkylphenols such as dodecylphenol, octylphenol, decylphenol and mixtures thereof and the like are also suitable alcohols for forming polyether polyols useful in the practice of the invention. Mono-alcohols, preferably mono-alcohols having from about 1 to about 18 carbon atoms, and alkoxy-substituted mono-alcohols such as methanol, ethanol, all isomers of propyl alcohol, all isomers of butyl alcohol, and ethers thereof are also suitable for forming hydroxy-functional polyethers.

Amines suitable for reaction with oxiranes to form polyethers include aliphatic and aromatic mono-amines, optionally having substituents such as alkyl, carboxyl, carboalkoxy substitution and the like. Exemplary aromatic amines include aniline, o-chloroaniline, p-phenylene diamine, 1,5-diaminonaphthalene, methylene dianiline, the condensation products of aniline and formaldehyde, 2,4-diamino toluene and the like. Exemplary aliphatic amines include methylamine, triisopropanolamine, isopropanolamine, diethanolamine, ethyenediamine, 1,3-propylenediamine, 1,4-propylenediamine, 1,4-butylenediamine, and the like and mixtures thereof. Amine based polyols are exemplified by those disclosed in U.S. Pat. No. 4,358,547.

The polyethers preferably have from an average of about 1 to about 8, preferably from about 2 to about 4 hydroxyl groups per molecule. The polyethers preferably have molecular weights ranging from about 88 to about 50,000, preferably from about 1000 to about 7500.

The polyethers may be prepared by processes known to those skilled in the art such as those processes described in *Encyclopedia of Chemical Technology*, Vol. 7, pp. 257–262, Interscience Publishers (1951); M. J. Schick, *Nonionic Surfactants*, Marcel Dekker, New York (1967); British Patent 898,306; and U.S. Pat. Nos. 1,922,459; 2,871,219; 2,891,073; and 3,058,921.

One or more catalysts are advantageously used in the preparation of the polyethers. Conventional catalysts include alkali or alkaline earth metals or their corresponding hydroxides and alkoxides, Lewis acids, mineral acids, and the like. One skilled in the art can readily determine suitable amounts of alkylene oxides, initiators, catalysts and adjuvants as well as suitable process conditions for polymerizing the alkylene oxides. Additional sources of detail regarding polymerization of alkylene oxides include J. Furukawa and T. Saegusa, "Polymerization of Aldehydes and Oxides," Interscience, New York (1963), pp. 125–208; G. Odian, "Principles of Polymerization," John Wiley & Sons, New York (2nd ed. 1970) pp. 512–521; J. McGrath, ed. "Ring-Opening Polymerization, Kinetics Mechanisms, and Synthesis," American Chemical Society, Washington, D.C. (1985) pp. 9–21, 137–147 and 204–217 and U.S. Pat. Nos. 2,716,137; 3,317,508; 3,359,217; 3,730,922; 4,118,426; 4,228,310; 4,239,907; 4,282,387; 4,3326,047; 4,446,313; 4,453,022; 4,483,941 and 4,540,828 which are incorporated herein by reference in their entirety.

Preferred catalysts include basic catalysts, more preferably hydroxides and alkoxides of alkali and alkaline earth metals, particularly cesium, sodium, potassium and lithium. Potassium hydroxide is more preferred. When alkoxides are used as catalysts, the alkoxy groups advantageously contain from about one to about 36 carbon atoms. Exemplary of such alkoxides are alkoxides having anions or propylene glycol, glycerine, dipropylene glycol, propoxylated propylene or ethylene glycols and the like.

When a basic catalyst is used in the preparation of a polyether, there is resulting basicity which is neutralized to preferably less than about 20 ppm, more preferably less than about 10 ppm, most preferably less than about 5 ppm hydroxide or alkoxide catalyst in the polyether.

In the process of the invention, the polyether, having its catalyst and water levels reduced to the preferred ranges, is then treated by being heated or cooled to a temperature suitable for acidic ion exchange resin catalyzed propenyl hydrolysis treatment and is passed through an acid ion exchange column, preferably upward through the ion exchange column in order to fluidize the ion exchange bed and avoid crushing the resin.

Ion exchange resins suitable for use in the practice of the invention include all acidic resins, such as ion exchange resins having carboxylic acid functionality, sulfonic acid functionality, and mixtures thereof. Preferably, the resin has sulfonic acid functionality. The resin preferably has an aqueous exchange capacity of about 0.5 to about 5, more preferably from about 1 to about 3 most preferably 1.5 to 2 equivalents/liter (of wet resin). Dry resin has about half the volume of wet resin. The term "aqueous exchange capacity" is defined as the number of equivalents of exchangeable ions per unit volume of resin. The aqueous exchange capacity can be obtained for acidic resins by titration with base in the presence of neutral salt.

While the ion exchange resin suitably has any backbone or substrate, it preferably has a styrene/divinyl benzene backbone. The amount of divinyl benzene is preferably from about 5 to about 15 weight percent. This amount of divinyl benzene results in crosslinking sufficient to form a gel or solid resin bead. Beads used in the practice of the invention are preferably gel beads. Gel beads are also known as microreticular resins, rather than macroreticular resins, and are advantageously produced in a suspension-type of polymerization wherein a monofunctional monomer such as styrene is polymerized with a fixed amount of bifunctional monomer such as divinylbenzene such that there is crosslinking at random positions. The beads are then functionalized by processes within the skill in the art. Preferably the beads are functionalized to produce sulfonic acid groups.

Acidic ion exchange resin beads are commercially available. Exemplary beads include certain Amberlite® ion exchange resins commercially available from Rohm and Haas Company such as Amberlite® 200, Amberlite® 252, Amberlite® 1R-118(H), Amberlite® IR-120 Plus (H), Amberlite® IRC-50 and certain DOWEX ion exchange resins commercially available from The Dow Chemical Company such as DOWEX® HGR W2-H, DOWEX® MSC-1-H, DOWEX® CCR-2 and the like. Preferred among these ion exchange resins are the gel resins which include DOWEX® HGR W2-H, DOWEX® HGR, DOWEX® HCR-W2, DOWEX® HCR-S, commercially available from The Dow Chemical Company, Amberlite® IR118, Amberlite® IR120, Amberlite® IR122 and Amberlite® IR124 commercially available from Rohm and Haas Company. The gel-type resins are preferred because longer useful resin life and less degradation of polyol is noted, particularly at higher temperatures; it is believed that gel-type resins have pores too small for the polyether molecules to enter and become trapped, and where the polyether may degrade.

The polyether is in contact with the resin for a time sufficient for the conversion of at least some of the the propenyl ethers to propionaldehyde, preferably at least about 30 seconds, more preferably from about 5 to about 60 minutes, most preferably from about 5 minutes to about 30 minutes. This contact time is controlled by the flow rate through a column and the volume of resin in that column. Achieving desired contact times is within the skill in the art without undue experimentation. Contact time is preferably balanced with temperature to avoid degradation of the polyether. Degradation can result in discoloration which is to be avoided.

Contact of resin and polyether suitably takes place at any temperature sufficient for the conversion of at least some of the the propenyl ethers to propionaldehyde at and, preferably, at a temperature at which degradation is avoided. Preferably the temperatures are from about 25° C. to about 200° C., more preferably from about 50° C. to about 125° C. Higher temperatures are preferably avoided when the resins are highly active such as fluorocarbon sulfonic acid resins and macroreticular resins. Weak acid carboxylic acid resins are preferably used at higher temperatures within the range, on the order of about 120° C., while sulfonic acid resins are suitable use over the entire range.

Contact is conveniently conducted at ambient pressure, but any pressure sufficiently high to maintain the reactants in a liquid phase and sufficiently low to avoid crushing the beads is suitable.

Contact of the polyether with the resin should take place in the presence of sufficient water for the conversion of propenyl ethers to aldehydes. Preferably there is at least an amount of water stoichiometric with the amount of propenyl ethers present in the polyol. More preferably there is at least a 25 fold excess of water. For instance, a triol having a molecular weight of about 3000, 0.01 meq/g of propenyl ether and 0.5 weight percent water, has a 28 fold excess of water. Water content of the polyol in contact with the resin preferably is at least about 0.1 weight percent, more preferably from about 0.1 to about 95 weight percent, most preferably from about 0.2 to about 10 weight percent, and even more preferably from about 0.5 to about 2 weight percent water in the polyether. Within these ranges, equipment used for polyether preparation and treatment determines what concentration of water is desirable. Certain equipment is more suitable for handling large volumes of water than is other equipment.

After ion exchange treatment, the polyether is preferably treated with an epoxy compound to reduce acidity. The acidity before treatment generally ranges from about 0.1 to about 30 ppm, more commonly from about 1 to about 2 ppm. Propionaldehyde and water concentrations are optionally reduced before or after treatment with an epoxy compound or mixture thereof. To avoid hydrolysis of epoxy compounds, water concentration is preferably less than about 2, more preferably from about 0.005 to about 2 weight percent in the polyether. Addition or reduction of water is within the skill in the art. For instance, vacuum stripping may be used to remove water.

Any inert epoxy compound, that is a compound which has at least one epoxy group and which is not detrimental to polyether stability, but which is effective to reduce the acidity of the polyether is suitably used in the practice of the invention. Suitable epoxy compounds include monoepoxy and polyepoxy compounds including alkylene oxides such as butylene oxide (all isomers), propylene oxide, ethylene oxide, styrene oxide and the like, as well as glycidyl ethers such as cresyl glycidyl ethers, phenylglycidyl ether and the like; epoxy resins, including those formed from epichlorohydrin and bisphenols, such as bisphenol A and bisphenol F and the like, as well as aliphatic and cycloaliphatic epoxy resin such as epoxycyclohexylmethyl epoxycyclohexyl carboxylates; cresol resins, Novolac resins and the like.

The epoxy compounds preferably have structures represented by Formula 1:

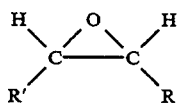

Formula I wherein R and R' (referred to hereinafter as R groups) are independently hydrogen, inert groups or R and R' together form an inert cyclic structure. Inert groups are groups which are not detrimental to polyether stability under conditions effective for treatment of polyethers to reduce acidity. Suitable inert groups include, for instance, additional epoxy groups, halogens, ester, alkyl, aryl, aralkyl, cycloalkyl, alkoxy, aryloxy, aralkoxy or cycloalkoxy groups, which groups are unsubstituted or inertly substituted, that is substituted by inert groups. Suitable halogens are chlorine, bromine, fluorine and iodine. R and R' together preferably have fewer than about 60 carbon atoms. When R and R' together form an inert cyclic structure, that structure is preferably a cyclohexyl ring having inert groups as substituents. Preferably, the weight percent oxirane oxygen in the epoxy compound is from about 3 to about 30, more preferably from about 6 to about 12 percent.

Epoxy compounds having more than one epoxy group preferably have molecular weights of from about 100 to about 1000. Preferred epoxy compounds are epoxy compounds other than the alkylene oxides used in preparation of the polyether, more preferably different from ethylene oxide, propylene oxides and butylene oxides, and include other monoepoxy compounds and epoxy resins. Epoxy resins, that is molecules having at least two glycidyl groups and which readily cure with amines, are particularly preferred.

The epoxy compounds are suitably used in amounts sufficient to reduce the acidity of the polyether, preferably from about 1 epoxy equivalent (eq)/10 Kg to about 1 epoxy eq/10,000 Kg polyether, more preferably from about 1 epoxy eq/50 Kg polyether to about 1 epoxy eq/2000 kg polyether, most preferably, from about 1 epoxy eq/1000 to about 1 epoxy eq/100 Kg polyether. The term "epoxy equivalent" as used herein means that amount of epoxy compound which contains an average of one epoxy group.

Contact of epoxy compound and polyether preferably occurs at a temperature sufficient for reaction of the epoxy compound to reduce acidity, but a temperature insufficient to result in undesirable degradation of the polyether. A sufficient temperature is preselected such that the acidity is reduced within a time acceptable for a specific application. Preferably, the temperature is from about 0° C. to about 150° C., more preferably from about 50° C. to about 135° C., most preferably from about 110° to about 130° C. These temperatures are suitably maintained for a time sufficient for the epoxy compound to react with acid, preferably for at least about 1 minute, more preferably for from about 20 to about 120 minutes.

Conditions suitable for reaction of the hydroxy-functional polyether with the epoxy compound are preferably avoided. For instance, catalysts for the reaction of epoxy compounds with the hydroxy-functional polyethers are preferably substantially absent, that is, if present the catalysts are present in insufficient quantities to result in reaction between the epoxy compounds and the hydroxy-functional polyethers (under the conditions of temperature and pressure to which the polyether is exposed) sufficient to interfere undesirably with acidity reduction or to measurably change physical properties of the polyether.

According to the present invention, the epoxy compound and polyether are admixed by the utilization of any mixing device. Local concentrations of epoxy compound are advantageously avoided, conveniently by thorough mixing. The mixing can be carried out batchwise or continuously in accordance with procedures within the skill in the art. Advantageously, in the described process, the epoxy compound is easily blended readily and intimately with the polyether.

After treatment with the epoxy compound, the polyether preferably has an acidity of less than about 5 ppm, more preferably less than about 1 ppm, most preferably less than about 0.1 ppm.

Hydroxy-functional polyethers having the concentration of unsaturated compounds, particularly propenyl ethers, reduced according to the practice of the invention are useful in preparing polyurethanes, particularly polyurethane foams which exhibit less scorch than do foams prepared from the same formulations but containing polyols not having their propenyl ether concentration so reduced. Such polyurethanes are referred to herein as scorch resistant polyurethanes. Furthermore, hydroxy-functional polyethers having both propenyl ether and acidity removed by the practice of the invention are similarly observed to be particularly useful in forming scorch resistant polyurethanes, preferably polyurethane foams. Compositions of the invention comprising hydroxy-functional polyethers and epoxy compounds are particularly useful for preparing scorch resistant polyurethanes, preferably foams. Relative scorch resistance, while generally subjective, is evident on visual observation by those skilled in the art. Preferably a sample of an inner portion of a commercial scale foam is observed. Scorch is also measured colorimetrically.

Those skilled in the art will recognize that the polyether purification processes of the invention are applicable as part of purification after polyether production or to purify polyethers which have propenyl ethers and/or acidity introduced by any means.

The following examples are offered to illustrate the invention, but are not intended to limit it. In each example, percentages are in weight percent unless otherwise stated. Examples of the invention are designated numerically, while comparative samples are designated alphabetically.

EXAMPLE 1

Reduction of Propenyl Ether in a Polyether Polyol Using a Sulfonic Acid Ion Exchange Resin A sample of 100 Kg of a polyether polyol having an average molecular weight of about 3100 and prepared from about 13 weight percent ethylene oxide and 87 weight percent propylene oxide with glycerine as an initiator (which polyol sample contains about 0.49 weight percent water and about 0.0066 milliequivalents (meq) propenyl ether per gram (g) of polyol) is fed by a positive displacement pump at a rate of 23 milliliters/minute (ml/min.) through a steam-heated heat exchanger to raise the temperature from 25° to 85°. The heated polyol is fed upward through a column of a water saturated (wet) gel-type polystyrene ion exchange resin which is crosslinked with about 10 weight percent divinylbenzene and sulfonated to 2.2 equivalents per liter of wet resin, to form a strongly acidic resin commercially available from The Dow Chemical Company under the trade designation DOWEX® HGR-W2-H. The column is one inch in diameter, 8 feet long and is heated by an electrical heating tape to a temperature inside the column of 88° C. The column is loaded with 660 mL of the wet ion exchange resin.

As the polyol passes through the ion exchange column, shrinkage of the ion exchange resin to about half its original volume is noted and is believed to be indicative of removal of water from the resin by the polyol. After the polyol passes through the column, its propenyl ether content is 0.00118 meq/g as determined by the method described in *Quantitative Organic Analysis via Functional Groups* by S. Siggia and J. G. Hanna, John Wiley and Sons, 1979 (reprinted 1988, Robert E. Krieger Pub.), p. 510–511. That method is also the one used to determine initial propenyl ether content.

For the analysis, a sample expected to contain about 0.0001 mole of propenyl ether is weighed in a 250 ml flask containing 50 mL of aqueous hydroxylamine hydrochloric acid reagent to form a mixture. The mixture is heated with mixing until the reaction is complete, about 0.5 hr at 80° C. After the reaction is complete, the mixture is titrated potentiometrically with 0.1N sodium hydroxide using silver/silver chloride and glass electrodes. The end point is detected from the recorded pH and volume data.

The reduction in propenyl ether shows that the acidic ion exchange resin is effective in reducing propenyl ether in a polyol.

EXAMPLES 2–3

Reduction of Propenyl Ether in Polyether Polyols Using a Sulfonic Acid Ion Exchange Resin The procedure used in Example 1 is repeated, using a glycerine initiated polyol having an average molecular weight of about 3500 and a composition of about 12 weight percent ethylene oxide units and 88 weight percent propylene oxide units in Example 2 and a glycerine initiated polypropylene polyol which is capped with about 14 weight percent ethylene oxide units and has an average molecular weight of about 4950 in Example 3. The ion exchange resin used in Example 1 is used in Examples 2 and 3.

The propenyl ether content of the polyol of Example 2 is reduced from 0.0066 to 0.00065. The propenyl ether content of the polyol of Example 3 is reduced from 0.014 to 0.0026. These data (measured at 85°–88° C.), show that the acidic ion exchange resin treatment is effective in removing propenyl ether from a variety of polyols.

EXAMPLE 4

Reduction of Propenyl Ether in Polyether Polyols Using a Macroporous Sulfonic Acid Ion Exchange Resin The procedure of Example 1 is repeated using as a polyether polyol having a molecular weight of about 3000 and prepared from about 93 weight percent propylene oxide and 7 weight percent ethylene oxide. A macroporous sulfonated polystyrene resin sulfonated to an exchange capacity of 1.6 eq/L on a wet basis is used; the resin is commercially available from The Dow Chemical Company under the trade designation DOWEX® MSC-1-H. The propenyl ether content of the polyol of Example 4 is reduced from 0.0115 to 0.0051 when treated at a temperature of 70°–85° C. with a residence time of 7 min.

EXAMPLE 5

Reduction of Propenyl Ether Using a Weak Acid Ion Exchange Resin

A gel-type weak acid resin composed of divinylbenzene and acrylic acid having an acid capacity of 3 eq/L on a wet basis commercially available from The Dow Chemical Company under the trade designation DOWEX® CCR-2 is mixed with 800 g of the polyol of Example 4 containing 0.02% water and is heated to 120° C. Samples are taken regularly and analyzed for propenyl ether as in Example 1.

The propenyl ether content of the polyol of Example 5 is reduced as shown below.

| Time (min.) | milliequivalents/ gram |
| --- | --- |
| Initial (o) | 0.00903 |
| 2 | 0.00425 |
| 4 | 0.00391 |
| 6 | 0.00331 |
| 10 | 0.00262 |
| 20 | 0.00203 |
| 30 | 0.00199 |

The results of Examples 4–5 show that these forms of ion exchange resins are capable of catalyzing the hydrolysis of propenyl ethers. The weak acid resin requires higher temperature, and longer contact time. It is noted that the macroporous resin gives some discoloration (yellowing) at higher temperatures.

EXAMPLE 6

Use of Various Epoxides to Further Purify Polyether Polyols

About 500 g of the polyol of Example 1 is treated as in Example 1 using a resin of the composition of the resin used in Example 1, except that the resin has a 750 micron particle size and dispersity of approximately one rather than having particle sizes of from about 100 to about 700 microns with an average particle size of 400 as in Example 1. A product containing water, polyether polyol and propionaldehyde is produced after treatment. The product is also found to have trace amounts of acidity. The product is heated to 110° C. at 10 torr to remove water and propionaldehyde. The resulting polyol has approximately 1 ppm of propionaldehyde and 500 ppm of water.

Propionaldehyde levels are determined by gas chromatography of the volatiles in the head space of a head space analysis vial, using the Hewlett Packard model HP-193 95A head space analyzer according to manufacturers' directions and using a 10 meter megabore capillary Carbowax® column commercially available from Union Carbide Corp. Water levels are determined by a Karl Fischer titration as described in ASTM D2849-69, Sections 61–70, reapproved 1980.

The resin-treated polyol is then heated to 85° C. and the epoxy compounds indicated in Table 1 are added at the concentrations indicated in Table 1 to form mixtures. The mixtures are shaken for 15 minutes each and then are left undisturbed at 100° C. for two hours. After the two hour period, the mixtures are cooled to room temperature, then a ten gram aliquot of each mixture is delivered into a headspace analysis vial, and analyzed as described previously. To each vial is added 15 microliters of 1-propenyl-2-hydroxy propyl ether. This enol ether has been found to adequately model propenyl ether end groups found in polyoxypropylene glycols. In the presence of acids and water, the enol ether is converted into propionaldehyde and 1,2-propylene glycol. Measurements of propionaldehyde, therefore, indirectly indicate amounts of acid present. Each mixture is tightly capped and placed in a head space analyzer oven at 90° C. for 18 hours. The head space is then analyzed for propionaldehyde by gas chromatography as were previous samples. Propionaldehyde generation is an indirect indication of the epoxy effectiveness in reacting with acids present.

The epoxy compounds used are: Epoxidized soybean oil having 6 to 7 weight percent oxirane oxygen, (indicated as "ESO"), prepared by the epoxidation of soybean oil, and commercially available from the Viking Chemical Company under the trade designation of VIKOFLEX 7170; an epoxy resin which is the reaction product of Bisphenol A and two moles of epichlorohydrin, commercially available from The Dow Chemical Company under the trade designation DOW EPOXY RESIN DER 330 (indicated as DER 330) having 9.5 weight percent oxirane oxygen; an epoxy resin which is the reaction product of hexapropylene glycol and two moles of epichlorohydrin, commercially available from The Dow Chemical Company under the trade name DOW EPOXY RESIN DER 732 (indicated as DER 732) having 6 percent oxirane oxygen; an epoxy resin which is the reaction product of tripropylene glycol and two moles of epichlorohydrin, commercially available from The Dow Chemical Company under the trade designation DOW EPOXY RESIN DER 736 (indicated as DER 736) having 8.8 percent oxirane oxygen; and (3,4-epoxycyclohexyl)methyl(3,4-epoxycyclohexyl)formate, commercially available from the Union Carbide Corporation under the trade designation of ERL-4221 (indicated as ERL-4221 or 4221) having 12.7 weight percent oxirane oxygen.

TABLE 1

| Sample # | Epoxy Compound Type | Amount of Epoxy compound used (ppm) | Propionaldehyde after treatment (ppm) | % Propionaldehyde Reduction |
|---|---|---|---|---|
| A (Control) | — | 0 | 56.2 | — |
| B (Control) | — | 0 | 52.2 | — |
| 6:1 | ESO | 50 | 0.4 | 99.3 |
| 6:2 | ESO | 200 | 0.3 | 99.4 |
| 6:3 | ESO | 500 | 0.2 | 99.6 |
| 6:4 | ESO | 1000 | 0.2 | 99.6 |
| 6:5 | DER-330 | 50 | 0.5 | 99.1 |
| 6:6 | DER-330 | 200 | 0.5 | 99.1 |
| 6:7 | DER-330 | 500 | 0.3 | 99.4 |
| 6:8 | DER-330 | 1000 | 0.3 | 99.4 |
| 6:9 | DER-732 | 50 | 0.5 | 99.1 |
| 6:10 | DER-732 | 200 | 0.4 | 99.3 |
| 6:11 | DER-732 | 500 | 0.3 | 99.4 |
| 6:12 | DER-732 | 1000 | 0.3 | 99.4 |
| 6:13 | DER-736 | 50 | 0.5 | 99.1 |
| 6:14 | DER-736 | 200 | 0.5 | 99.1 |
| 6:15 | DER-736 | 500 | 0.3 | 99.4 |
| 6:16 | DER-736 | 1000 | 0.3 | 99.4 |
| 6:17 | ERL-4221 | 50 | 0.4 | 99.3 |
| 6:18 | ERL-4221 | 200 | 0.4 | 99.3 |
| 6:19 | ERL-4221 | 500 | 0.2 | 99.6 |
| 6:20 | ERL-4221 | 1000 | 0.2 | 99.6 |

The data in Table 1 indicates that PA generation is inhibited as much as 99.6% by addition of the epoxide compounds.

EXAMPLE 7

Larger Scale Epoxide Treatment

Samples of the polyol of Example 1 treated with the ion exchange resin as described in Example 6 are treated with varying levels of the epoxy compounds indicated in Table 2 (as identified in Example 6) to form mixtures. To these mixtures are then added 1 or 5 weight percent (as indicated in Table 2) of a second polyol, the polyol of Example 3, which has not been treated with an ion exchange resin and contains known levels of propenyl ethers. The mixtures are aged for 43 hours at 50° C. Propionaldehyde concentration is measured as in Example 6 and results are shown in Table 2.

TABLE 2

| Sample # | Epoxy Type | Epoxy Level | Wt. % V-4701 | ppm propionaldehyde Generation | wt % of propionaldehyde Reduction |
|---|---|---|---|---|---|
| C (Control) | — | 0 | 1 | 2.2 | — |
| 7:1 | DER 736 | 100 | 1 | 0.5 | 77.3 |
| 7:2 | DER 736 | 500 | 1 | 0.3 | 86.4 |
| 7:3 | DER 736 | 1000 | 1 | 0.2 | 90.9 |
| D (Control) | — | 0 | 5 | 13.7 | — |
| 7:4 | DER 736 | 100 | 5 | 0.4 | 97.1 |
| 7:5 | DER 736 | 500 | 5 | 0.2 | 98.5 |
| 7:6 | DER 736 | 1000 | 5 | 0.1 | 99.3 |
| 7:7 | ERL-4221 | 100 | 1 | 0.7 | 68.2 |
| 7:8 | ERL-4221 | 500 | 1 | 0.2 | 90.9 |
| 7:9 | ERL-4221 | 1000 | 1 | 0.1 | 95.4 |
| 7:10 | ERL-4221 | 100 | 5 | 0.2 | 98.5 |
| 7:11 | ERL-4221 | 500 | 5 | 0.1 | 99.3 |
| 7:12 | ERL-4221 | 1000 | 5 | 0.1 | 99.3 |

The data in Table 2 shows that acid catalyzed propionaldehyde generation is reduced by addition of epoxy compounds to a polyether containing propenyl ethers. These results are consistent with those of the smaller scale samples in Example 6, wherein added 1-propenyl, 2-hydroxy propyl ether provides model propenyl groups.

EXAMPLE 9

Kinetic Data on the Epoxide Treatment of Acid Ion Exchange Treated Polyether Polyols A sample of the polyether polyol used in Example 1 and ion exchange treated as in Example 1 is heated to 100° C. with stirring and treated with 500 ppm of epoxy resin commercially available from the Dow Chemical Company under the trade designation, DOW EPOXY RESIN DER 736. Time t=0 is taken as the point of epoxy addition. At time periods ranging from 2 to 60 minutes, a 60 mL aliquots are taken from the mixture, 50 mL of each is titrated for acid (direct assessment of acid scavenging). To the remaining 10 mL is added 5% by wt. of the second polyol of Example 8 which is not treated with an ion exchange resin to act as a source of propionaldehyde (indirect assessment of acid scavenging). This sample is oven aged at 100° C. for 24 hours and then analyzed for propionaldehyde as in Example 7. Table 3 shows the results of these experiments.

TABLE 3

| Sample # | Temp. °C. | Time (min.) | Titrated Acidity (ppm) | ppm propionaldehyde |
|---|---|---|---|---|
| 8:1 | 50 | 0 | 1.9 | — |
| 8:2 | 50 | 5 | — | 13.9 |
| 8:3 | 50 | 15 | 1.2 | 13.6 |
| 8:4 | 50 | 30 | 1.0 | 11.8 |
| 8:5 | 50 | 60 | 0.7 | 9.1 |
| 8:6 | 50 | 120 | 0.1 | 3.7 |
| 8:7 | 50 | 210 | non-detectable | 2.4 |
| 8:8 | 100 | 2 | 0.8 | 16.5 |
| 8:9 | 100 | 5 | non-detectable | 4.4 |
| 8:10 | 100 | 15 | non-detectable | 1.1 |
| 8:11 | 100 | 30 | non-detectable | 0.7 |
| 8:12 | 100 | 60 | non-detectable | 0.0 |

The data in Table 3 shows that acids are adequately removed by the epoxides at 100° C., as well as at 50° C., but more time is required at the lower temperature.

EXAMPLE 10

Use of a Commercial Scale Ion Exchange Column

An ion exchange column measuring 11 feet in diameter and 16 feet high is loaded with 400 cubic feet ($ft^3$) [equivalent to 200 $ft^3$ of dry resin] of water saturated ion exchange resin of these type used in Example 1. The polyol of Example 2, having a water content of 0.5 weight percent, is flowed upward through the column at a rate of 100 gallons per minute while a temperature of 85° C. is maintained. This flow rate allows a contact time of 15 minutes. This flow is maintained for 5 days, then the polyol is changed to the polyol of Example 1, but other conditions are kept constant.

Samples of polyol entering and exiting the column are taken daily and analyzed for propenyl ethers as in Example 1. The results are tabulated in Table 4.

TABLE 4

| Time (days) | Propenyl ethers meq/gm (in) | Propenyl ethers meq/gm (out) | Conv % |
|---|---|---|---|
| 1 | 0.005 | 0.00203 | 59 |
| 2 | 0.00384 | 0.0007 | 82 |
| 3 | 0.0038 | 0.0006 | 84 |
| 4 | 0.00431 | 0.0006 | 86 |
| 5 | 0.0035 | 0.0006 | 83 |
| 6 | 0.0033 | 0.0006 | 82 |
| 7 | 0.00342 | 0.0006 | 82 |
| 8 | 0.00363 | 0.0007 | 81 |
| 9 | 0.00345 | 0.0006 | 83 |
| 10 | 0.00354 | 0.0007 | 80 |

These data show that ion exchange treatment is effective in reducing propenyl ether concentration on a large scale for at least 10 days.

What is claimed is:

1. A process for reducing the concentration of propenyl ethers in a hydroxy-functional polyether having oxypropylene units by a process comprising the steps of:
   (1) contacting the polyether with an acidic ion exchange resin, wherein the ion exchange resin has exchange groups having acid functionality, for a time and at a temperature sufficient for the conversion of at least some of the propenyl ethers to propionaldehyde and in the presence of sufficient water for the conversion; and thereafter
   (2) treating the polyether with an epoxy compound in an amount sufficient to reduce the acidity of the polyol.

2. The process of claim 1 wherein the acid ion exchange resin is a gel-type resin.

3. The process of claim 2 wherein the acid ion exchange resin is prepared from a mixture of styrene and divinylbenzene, the divinylbenzene being present in an amount of from about 5 to about 15 weight percent based on mixture weight.

4. The process of claim 3 wherein the acid ion exchange resin has a ion exchange capacity of from about 0.5 to about 5 equivalents per liter of wet resin.

5. The process of claim 4 wherein the acid ion exchange resin has a ion exchange capacity of from about 1 to about 3 equivalents per liter of wet resin.

6. The process of claim 5 wherein step (1) takes place in the presence of from about 0.5 to about 2 weight percent water based on polyether, at a temperature of from about 50 to about 125° C., with an upward flow of polyether through the resin and with at least a 30 second contact time between resin and polyether.

7. The process of claim 5 wherein the epoxy compound has an oxirane oxygen content of from about 3 to about 30 weight percent.

8. The process of claim 7 wherein the epoxy compound is an epoxy resin having a molecular weight of from about 100 to about 1000.

9. The process of claim 7 wherein the epoxy compound is used in an amount of from about 1 epoxy equivalent/10,000 kg polyether to about 1 epoxy equivalent/10 kg polyether.

10. The process of claim 9 wherein the epoxy compound is used in an amount of from about 1 epoxy equivalent/1000 kg polyether to about 1 epoxy equivalent/100 kg polyether.

11. The process of claim 9 wherein the acidity is reduced to less than about 5 ppm in the polyether.

12. The process of claim 11 wherein the acidity is reduced to from about 0.1 ppm to about 1 ppm in the polyether.

13. The process of claim 12 wherein step (2) takes place in the presence of water and at a temperature of from about 50° to about 135° C.

14. The process of claim 9 wherein the epoxy compound has an oxirane oxygen content of from about 6 to about 12 weight percent.

* * * * *